United States Patent [19]

Nishikawa et al.

[11] Patent Number: 4,460,783
[45] Date of Patent: Jul. 17, 1984

[54] ETHER IMIDES AND PROCESS FOR PRODUCING THE SAME

[75] Inventors: Akio Nishikawa; Masashi Shitara; Susumu Era, all of Hitachi; Toshiaki Fukushima, Ichihara; Hiroshi Suzuki, Hitachi; Hisashi Kohkame, Narashino, all of Japan

[73] Assignee: Hitachi, Ltd., Tokyo, Japan

[21] Appl. No.: 226,029

[22] Filed: Jan. 19, 1981

[30] Foreign Application Priority Data

Jan. 21, 1980 [JP] Japan .................................. 55-4636

[51] Int. Cl.³ .......................................... C07D 209/56
[52] U.S. Cl. .................................... 548/549; 548/435; 548/462; 548/544; 548/545; 548/548
[58] Field of Search ............ 260/326, 5 FM; 562/441; 546/190; 548/435, 462, 549, 544, 545, 548

[56] References Cited

U.S. PATENT DOCUMENTS 2,462,835 5/1949 Arnold et al. .
2,818,405 12/1957 Kovaeic .
3,562,223 2/1971 Bargain et al. .

Primary Examiner—Allan Lieberman
Attorney, Agent, or Firm—Antonelli, Terry and Wands

[57] ABSTRACT

An ether imide of the formula:

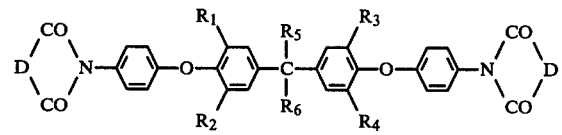

wherein $R_1$, $R_2$, $R_3$, $R_4$, $R_5$, $R_6$ and D are as defined in the specification produced by reacting a diamine with an ethylenically unsaturated dicarboxylic acid can give a composition together with one or more unsaturated polyesters, epoxy compounds, amines, and the like to give shaped articles excellent in flexibility and heat resistance.

13 Claims, No Drawings

ETHER IMIDES AND PROCESS FOR PRODUCING THE SAME

This invention relates to an ether imide which is useful as an intermediate for producing polymers, a process for producing the same and a composition including the same.

Heretofore, as raw materials for heat resistant polymers, there have been known N,N'-substituted bismaleimides obtained from maleic anhydride and a diamine, reaction products of maleic anhydride with aniline resin, and the like materials (e.g., U.S. Pat. Nos. 2,462,835, 2,818,405, 3,562,223). But these imides are good in heat resistance, but they have some disadvantages in that it is difficult to give flexibility to them, and their solubilities in a solvent such as acetone, toluene, etc., are not good.

It is an object of this invention to provide an ether imide which is useful as an intermediate for producing polymers excellent in heat resistance and flexibility, a process for producing the same and a composition including the same.

The ether imide of this invention is characterized by having the formula:

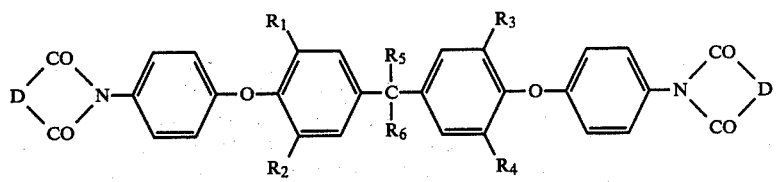

wherein $R_1$, $R_2$, $R_3$ and $R_4$ are independently hydrogen, a lower alkyl group, a lower alkoxy group, chlorine or bromine; $R_5$ and $R_6$ are independently hydrogen, a methyl group, an ethyl group, a trifluoromethyl group or a trichloromethyl group; and D is a bivalent organic group having 2 to 24 carbon atoms.

In the above definitions, the term "lower alkyl" means an alkyl group having preferably 1 to 6 carbon atoms, the term "lower alkoxy" means an alkoxy group having preferably 1 to 6 carbon atoms, and the term "bivalent organic group" means an ethylenically unsaturated group such as

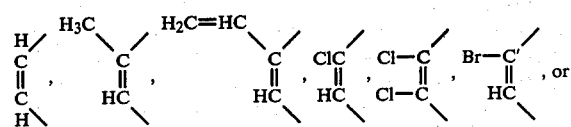

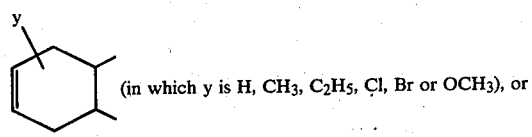 (in which y is H, CH$_3$, C$_2$H$_5$, Cl, Br or OCH$_3$), or

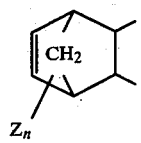

(in which Z is H, CH$_3$, or a halogen atom and n is an integer of 1 to 4).

The ether imide of the formula (I) can be prepared by reacting a diamine having ether linkages represented by the formula:

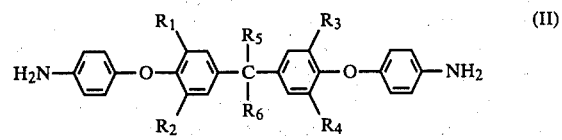

wherein $R_1$, $R_2$, $R_3$, $R_4$, $R_5$ and $R_6$ are as defined above, with an ethylenically unsaturated dicarboxylic acid anhydride of the formula:

wherein D is as defined above.

The ether imide of the formula (I) has characteristic absorptions at 1710 cm$^{-1}$ and 1780 cm$^{-1}$ based on the imide linkage and at 1230 cm$^{-1}$ based on the ether linkage in infrared absorption spectra.

Examples of the diamines having ether linkages (II) are 2,2-bis[4-(4-aminophenoxy)phenyl]propane, 2,2-bis[3-(methyl-4-(4-aminophenoxy)phenyl]propane, 2,2-bis[3-chloro-4-(4-aminophenoxy)phenyl]propane, 2,2-bis[3-bromo-4-(4-aminophenoxy)phenyl]propane, 2,2-bis[3-ethyl-4-(4-aminophenoxy)phenyl]propane, 2,2-bis[3-propyl-4-(4-aminophenoxy)phenyl]propane, 2,2-bis[3-isopropyl-4-(4-aminophenoxy)phenyl]propane, 2,2-bis[3-butyl-4-(4-aminophenoxy)phenyl]propane, 2,2-bis[3-sec-butyl-4-(4-aminophenoxy)phenyl]propane, 2,2-bis[3-methoxy-4-(4-aminophenoxy)phenyl]propane, 1,1-bis[4-(4-aminophenoxy)phenyl]ethane, 1,1-bis[3-methyl-4-(4-aminophenoxy)phenyl]ethane, 1,1-bis[3-chloro-4-(4-aminophenoxy)phenyl]ethane, 1,1-bis[3-bromo-4-(4-aminophenoxy)phenyl]ethane, bis[4-(4-aminophenoxy)phenyl]methane, bis[3-methyl-4-(4-aminophenoxy)phenyl]methane, bis[3-chloro-4-(4-aminophenoxy)phenyl]methane, bis[3-bromo-4-(4-aminophenoxy)phenyl]methane, 1,1,1,3,3,3-hexafluoro-2,2-bis[4-(4-aminophenoxy)phenyl]propane, 1,1,1,3,3,3-hexachloro-2,2-bis[4-(4-aminophenoxy)phenyl]propane, 3,3-bis[4-(4-aminophenoxy)phenyl]pentane, 1,1-bis[4-(4-aminophenoxy)phenyl]propane, 1,1,1,3,3,3-hexafluoro-2,2-bis[3,5-dimethyl-4-(4-aminophenoxy)-phenyl]propane, 1,1,1,3,3,3-hexafluoro-2,2-bis[3,5-dibromo-4-(4-aminophenoxy)phenyl]propane, 1,1,1,3,3,3-hexafluoro-2,2-bis[3-methyl-4-(4-aminophenoxy)phenyl]propane, 2,2-bis[4-(4-aminophenoxy)-phenyl]trifluoromethylpropane, and the like.

As the ethylenically unsaturated dicarboxylic acid anhydride of the formula (III), there can be used at least one of maleic anhydride, citraconic anhydride, itaconic anhydride, pyrocinchonic anhydride, dichloromaleic anhydride, and the products of Diels-Alder reaction between at least one of these anhydrides mentioned above and at least one cyclodiene such as pentacyclodiene, hexacyclodiene, or the like, tetrahydrophthalic anhydride, methyltetrahydrophthalic anhydride, ethyltetrahydrophthalic anhydride, chlorotetrahydrophthalic anhydride, bromotetrahydrophthalic anhydride, methoxytetrahydrophthalic anhydride, endomethylenetetrahydrophthalic anhydride and methylendomethylenetetrahydrophthalic anhydride.

The reaction between the diamine of the formula (II) and the ethylenically unsaturated carboxylic acid anhydride of the formula (III) can preferably be carried out by the following two steps: the first step comprising contacting the diamine of the formula (II) with the ethylenically unsaturated dicarboxylic acid anhydride of the formula (III) in an organic solvent at a temperature of $-10°$ to $+40°$ C. for 0.5 to 10 hours to give an ether amic acid of the formula:

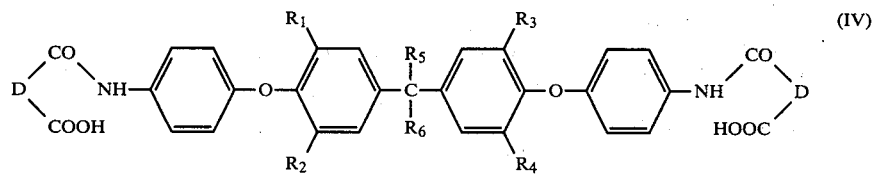

wherein $R_1$, $R_2$, $R_3$, $R_4$, $R_5$, $R_6$ and D are as defined above, and the second step comprising subjecting the ether amic acid of the formula (IV) to ring closing dehydration to form imide rings.

Examples of the organic solvent used in the first step are dimethyl formamide, dimethyl acetamide, dimethyl sulfoxide, N-methyl-pyrrolidone, N-methyl caprolactam, tetrahydrofuran, dioxane, acetone, diethyl ketone, methyl ethyl ketone, toluene and the like.

The thus obtained ether amic acid of the formula (IV) is a stable intermediate and can be used as a starting material for producing the ether imide of the formula (I).

The ring closing dehydration of the ether amic acid of the formula (IV) in the second step can be carried out by using an anhydrous substance for dehydration such as acetic anhydride, propionic anhydride, butyric anhydride, and the like in an amount of 1.05 to 1.5 moles per mole of the amic acid group, and adding a tertiary amine such as triethylamine, benzyldimethylamine, or the like in an amount of 0.15 to 0.5 mole per mole of the amic acid group in the presence of a catalyst such as nickel acetate, lithium acetate, potassium acetate, sodium acetate, calcium acetate, or the like in an amount of 0.5 to 0.05 mole per mole of the amic acid group and in a solvent such as acetone, N-methyl-2-pyrrolidone, toluene or the like or in the absence of a solvent, at a temperature of 60° to 120° C. for about 0.5 to 3 hours.

The ether imide of the formula (I) can be modified by adding at least one polymerizable monomer having at least one

group of a vinyl, allyl or acryl type. Examples of such monomers are styrene, vinyltoluene, α-methylstyrene, divinyl benzene, diallyl phthalate, diallyl phthalate prepolymer, chlorostyrene, dichlorostyrene, bromostyrene, dibromostyrene, diallylbenzene phosphate, diallylaryl phosphiric acid esters, acrylic acid, acrylic esters, methacrylic acid, methacrylic esters, triallyl cyanurate, triallyl cyanurate prepolymer, tribromophenol allyl ether, and the like. These monomers can be used alone or as a mixture thereof.

The ether imide of the formula (I) can be modified by adding at least one resin or compound before curing. In other words, this invention also provide a composition comprising the ether imide of the formula (I) and at least one resin or compound such as an unsaturated polyester, a vinyl ester resin, a polyamine, an epoxide, a phenolic resin, and the like.

In the case of using an unsaturated polyester, 0.1 to 10 parts by weight of the unsaturated polyester can be mixed with 1 part by weight of the ether imide of the formula (I). The unsaturated polyester preferably usable in this invention is a mixture comprising (a) a polyester resin containing unsaturated groups prepared by condensation or addition polymerization using esterification, ester interchange reaction or the like of one or more unsaturated dibasic acids, saturated dibasic acids and their anhydrides or their lower alkyl esters, and diols or alkylene monoxides and their derivatives in the presence or absence of a catalyst, (b) an ethylenic polymerizable monomer containing at least one vinyl group, allyl group or the like, and (c) a peroxide catalyst. The unsaturated polyester composition may further contain a vinyl ester type resin obtained by reacting an epoxy compound such as bisphenol A type, novolac type, or the like with methacrylic acid or acrylic acid. Examples of the above-mentioned unsaturated dibasic acids and saturated dibasic acids as the acid component are maleic acid, maleic anhydride, fumaric acid, chloromaleic acid, dichloromaleic acid, citraconic acid, citraconic anhydride, mesaconic acid, itaconic acid, succinic acid, adipic acid, sebacic acid, azelaic acid, phthalic acid, phthalic anhydride, isophthalic acid, terephthalic acid, methylglutanic anhydride, pimelic acid, hexahydrophthalic acid, hexahydrophthalic anhydride, tetrahydrophthalic acid, carbic anhydride, Het Acid, Het Anhydride, tetrachlorophthalic acid, tetrachlorophthalic anhydride, tetrabromophthalic acid, tetrabromophthalic anhydride, and the like. Lower alkyl esters of these unsaturated and saturated acids can also be used as the acid component. Examples of diols and alkylene oxides as the alcohol component are ethylene glycol, diethylene glycol, triethylene glycol, polyethylene glycol, propylene glycol, dipropylene glycol, trimethylene glycol, tetramethylene glycol, hexamethylene glycol, 2,2-diethyl-propanediol, 1,3-neopentyl glycol, dibromoneopentyl glycol, bisphenol dioxydiethyl ether, hydrogenated bisphenol A, 2,2-di(4-hydroxypropoxyphenyl)propane, ethylene oxide, propylene oxide, 3,3,3-trichloropropylene oxide, 2-methyl-3,3,3-trichloropropylene oxide, phenyl glycidyl ether, allyl glycidyl ether, and the like. If required, tri- or higher functional polybasic acids and/or polyhydric alcohols can be used together unless they give bad influence on the effects of this invention. As crosslinking agent, there can be used styrene, vinyltoluene, α-methylstyrene, divinyl benzene, diallyl phthalate, diallyl phthalate prepolymer, chlorostyrene, dichlorostyrene, bromostyrene, dibromostyrene, diallylbenzene phosphonate, diallylaryl phosphiric acid ester, triallyl cyanurate, triallyl cyanurate prepolymer, tribromophenol allyl ether, and the like. Needless to say, two or more compounds mentioned above can be used for producing the unsaturated polyester as the acid component, the alcohol component and the crosslinking agent. Further various modifying processes can be used and various modifying agents can be added thereto. In addition, two or more unsaturated polyesters can be used in the abovementioned composition.

A composition comprising 1 part by weight of the ether imide of the formula (I) and 0.1 to 10 parts by weight of one or more amines such as polyamines, particularly diamines, gives excellent flexibility and heat resistance to shaped articles. Examples of the amines are m-phenylenediamine, p-phenylenediamine, benzidine, 3,3'-dimethyl-4,4'-diaminobiphenyl, 3,3'-dichlorobenzidine, 3,3'-dimethoxybenzidine, 4,4'-diaminodiphenylmethane, 1,1-bis(4-aminophenyl)ethane, 2,2-bis(4-aminophenyl)propane, 2,2-bis(4-aminophenyl)hexafluoropropane, 2,2-bis(4-aminophenyl)-1,3-dichloro-1,1,3,3-tetrafluoropropane, 4,4'-diaminodiphenyl ether, 4,4'-diaminodiphenyl sulfide, 3,3'-diaminodiphenyl sulfide, 4,4'-diaminodiphenyl sulfoxide, 4,4'-diaminodiphenyl sulfone, 3,3'-diaminodiphenyl sulfone, 3,3'-diaminodibenzophenone, 4,4'-diaminobenzophenone, 3,4'-diaminobenzophenone, N,N-bis(4-aminophenyl)methylamine, N,N-bis(4-aminophenyl)-n-butylamine, N,N-bis(4-aminophenyl)amine, m-aminobenzoyl-p-aminoanilide, 4-aminophenyl-3-aminobenzoate, 4,4'-diaminoazobenzene, 3,3'-diaminoazobenzene, bis(4-aminophenyl)diethylsilane, bis(4-aminophenyl)phenyl phosphine oxide, bis(4-aminophenyl)ethyl phosphine oxide, 1,5-diaminonaphthalene, 2,6-diaminopyridine, 2,5-diamino-1,1,4-oxadiazole, m-xylylenediamine, p-xylylenediamine, 2,4-(p-β-amino-t-butylphenyl) ether, p-bis-2-(2-methyl-4-aminopentyl)benzene, p-bis(1,1-dimethyl-5-aminopentyl)benzene, hexamethylenediamine, heptamethylenediamine, octamethylenediamine, nonamethylenediamine, decamethylenediamine, 2,11-diaminododecane, 1,12-diaminooctadecane, 2,2-dimethylpropylenediamine, 2,5-dimethylenehexamethylenediamine, 3-methylheptamethylenediamine, 2,5-dimethylheptamethylenediamine, 4,4-dimethylheptamethylenediamine, 5-methylnonamethylenediamine, 1,4-diaminocyclohexane, bis(p-aminocyclohexyl)methane, 3-methoxyhexamethylenediamine, 1,2-bis(3-aminopropoxy)ethane, bis(3-aminopropyl)sulfide, N,N-bis(3-aminopropyl)methylamine, and the like. There can also be used N-aryl substituted aromatic triamines such as 2,4-diaminodiphenylamine, 2,4-diamino-5-methyldiphenylamine, 2,4-diamino-4'-methyldiphenylamine, 1-amino-2,4-diaminonaphthalene, 3,3'-diamino-4-anilinobenzophenone, and the like. Further, a polyamine of the formula:

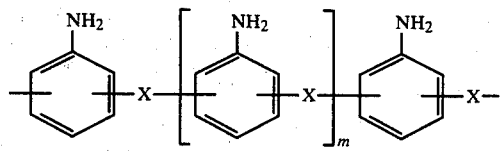

wherein X is an alkylidene group including a methylene group, and m is 0.1 or more on an average, is also useful. Particularly effective compounds for providing flexibility are diamines having ether linkages represented by the formula (II), for example, 2,2-bis[4-(4-aminophenoxy)phenyl]propane, 2,2-bis[3-methyl-4-(4-aminophenoxy)phenyl]propane, and the like.

A composition comprising 1 part by weight of the ether imide of the formula (I) and 0.1 to 10 parts by weight of one or more epoxy compounds has excellent molding processability and gives highly heat resistant cured articles. Examples of epoxy compounds are bifunctional epoxy compounds such as glycidyl ether of bisphenol A, butadiene diepoxide, 3,4-epoxycyclohexylmethyl-(3,4-epoxy)cyclohexane carboxylate, vinylcyclohexane dioxide, 4,4'-di(1,2-epoxyethyl)diphenyl ether, 2,2'-bis(3,4-epoxycyclohexyl)propane, glycidyl ether of resorcinol, diglycidyl ether of phloroglucinol, diglycidyl ether of methylphloroglucinol, bis(2,3-epoxycyclopentyl)ether, 2-(3,4-epoxy)cyclohexane-5,5-spiro(3,4-epoxy)cyclohexane-m-dioxane, bis(3,4-epoxy-6-methylcyclohexyl) adipate, N,N'-m-phenylene-bis(4,5-epoxy-1,2-cyclohexanedicarboxyimide), etc.; tri- or higher polyfunctional epoxy compounds such as triglycidyl ether of para-aminophenol, polyallyl glycidyl ether, 1,3,5-tris(1,2-epoxyethyl)benzene, 2,2',4,4'-tetraglycidoxy benzophenone, polyglycidyl ether of phenol-formaldehyde novolac resin, triglycidyl ether of trimethylol propane, etc.; halogenated epoxy compounds such as brominated epoxides; hydantion epoxy compounds; and the like.

A composition comprising the ether imide of the formula (I) and a phenol-formaldehyde condensate with or without one or more epoxy compounds increases the molding processability and can easily be dissolved in a solvent, which makes possible to use such a composition for casting.

A composition comprising the ether imide of the formula (I) and one or more triallyl cyanurate or triallyl cyanurate prepolymer is also effective.

The above-mentioned compositions can be used for varnishes, molding materials, and the like. When the above-mentioned compositions are used as varnishes, at least one of these compositions is dissolved in a conventionally used organic solvent in an amount of 5% by weight or more, preferably 50–70% by weight or less.

Cured resins having good properties such as flexibility, heat resistance can be obtained by heating these resin compositions at a temperature of e.g., 100°–300° C. or 100°–250° C. Since these compositions can give articles excellent in flexibility and heat resistance after cured, they are useful as electrical insulating materials.

This invention is illustrated by way of the following Examples, in which all parts and percents are by weight unless otherwise specified.

EXAMPLE 1

2,2-Bis[4-(4-aminophenoxy)phenyl]propane in an amount of 20 parts was dissolved in 200 parts of acetone and 10 parts of maleic anhydride was added thereto. After reacting at 5° C. or lower with stirring for 3 hours, 10 parts of acetic anhydride and 0.05 part of potassium acetate were added to the reaction solution and the reaction was carried out at 80°-100° C. for about 1 hour. After filtration, washing and drying, 17.5 parts of ether imide (a) was obtained.

The ether imide (a) had characteristic absorptions at 1230-1240 cm$^{-1}$ due to the ether linkage and at 1715 cm$^{-1}$ and 1780 cm$^{-1}$ due to the imide linkage in IR spectrum.

EXAMPLE 2

2,2-Bis[3-methyl-4-(4-aminophenoxy)phenyl]propane in an amount of 42 parts was dissolved in 500 parts of acetone and 20 parts of maleic anhydride was added thereto. The reaction was carried out at 5° C. or lower with stirring for 2 hours under a nitrogen stream. Subsequently, 30 parts of acetic anhydride and 0.05 part of lithium acetate were added to the reaction solution and the reaction was carried out at 80°-100° C. for about 1 hour. After filtration, washing and drying, 55 parts of ether imide (b) was obtained.

The ether imide (b) had characteristic absorptions at 1235 cm$^{-1}$ due to the ether linkage and at 1720 cm$^{-1}$ and 1780 cm$^{-1}$ due to the imide linkage in IR spectrum.

EXAMPLES 3 TO 6

Compositions containing the ether imide (a) obtain in Example 1 or the ether imide (b) obtained in Example 2 and an unsaturated polyester (isophthalic acid-maleic anhydride-glycol), 4,4'-diaminodiphenylmethane, or a novolac type epoxy compound (epoxy equivalent 225) in amounts as listed in Table 1 were prepared. To each composition, 70% of silica glass powder as a filler, 2 parts of stearic acid as a mold release agent, and 1 part of carbon black as a colorant were added and mixed uniformly in a kneader.

Samples were produced by curing these mixtures at 150°-170° C. for 1-5 minutes with heating under a pressure of 70 kg/cm$^2$ and physical properties of these samples were tested. The results are as shown in Table 1.

TABLE 1

| | Examples | | | |
|---|---|---|---|---|
| | 3 | 4 | 5 | 6 |
| Composition (parts) | | | | |
| Ether imide (a) | 100 | 100 | — | 100 |
| Ether imide (b) | — | — | 20 | — |
| Unsaturated polyester | 100 | — | — | — |
| 4,4'-Diaminodiphenylmethane | — | 100 | — | 200 |
| Epoxy compound | — | — | 100 | — |
| Dicumyl peroxide | 3 | — | — | — |
| Properties | | | | |
| Glass transition temp. (°C.) | 185 | 225 | 198 | 218 |
| Flexural strength at 180° C. *1 (kg/cm$^2$) | 420 | 575 | 570 | 570 |
| Retention of flexural strength, after 30 days at 200° C. (%) | 85 | 100 | 100 | 100 |
| Bending strain (%) *2 | 6.7 | 5.2 | 3.2 | 4.7 |

(Note)
*1 and *2: Distance between the supports 80 mm Head speed 1 mm/min

EXAMPLE 7

2,2-Bis[3-ethyl-4-(4-aminophenoxy)phenyl]propane in an amount of 40 parts was dissolved in 500 parts of acetone and 18 parts of maleic anhydride dissolved in acetone was added thereto. The reaction was carried out at 5° C. or lower with stirring for 1 hour under a nitrogen stream. Subsequently, 150 parts of acetic anhydride and 1 part of sodium acetate were added to the reaction solution and the reaction was carried out at room temperature or higher for about 1 hour. After filtration, washing and drying, 42.5 parts of ether imide (c) was obtained.

The ether imide (c) had characteristic absorptions at 1235-1240 cm$^{-1}$ due to the ether linkage and at 1710 cm$^{-1}$ and 1780 cm$^{-1}$ due to the imide linkage in IR spectrum.

EXAMPLE 8

2,2-Bis[4-(4-aminophenoxy)phenyl]propane in an amount of 20 parts was dissolved in 200 parts of acetone and 15 parts of tetrahydrophthalic anhydride dissolved in acetone was added thereto. The reaction was carried out at 5° C. or lower for about 2 hours under nitrogen stream with stirring. Subsequently 100 parts of acetic anhydride and 0.5 part of potassium acetate were added to the reaction solution and the reaction was carried out at room temperature or higher for about 1 hour. After filtration, washing and drying, 32 parts of ether imide (d) was obtained.

The ether imide (d) had characteristic absorptions at 1230-1240 cm$^{-1}$ due to the ether linkage and at 1710 cm$^{-1}$ and 1780 cm$^{-1}$ due to the imide linkage.

EXAMPLES 9 TO 13

Compositions containing the ether imide (c) or (d) and an unsaturated polyester (isophthalic acid-maleic anhydride-glycol), triallyl cyanurate, triallyl cyanurate prepolymer, or a novolac type epoxy compound (epoxy equivalent 225) and a catalyst, if necessary, in amounts as listed in Table 2 were prepared. Further the same additives as used in Examples 3 to 6 were added to each composition and samples were molded under the same conditions as used in Examples 3 to 6. The results are as shown in Table 2.

TABLE 2

| | Examples | | | | |
|---|---|---|---|---|---|
| | 9 | 10 | 11 | 12 | 13 |
| Composition (parts) | | | | | |
| Ether imide (c) | 100 | 100 | 100 | — | — |
| Ether imide (d) | — | — | — | 100 | 100 |
| Unsaturated polyester | 35 | — | — | — | 70 |
| Triallyl cyanurate | 35 | — | 30 | 50 | — |
| Triallyl cyanurate prepolymer | — | 60 | — | — | — |
| Epoxy compound | — | — | 200 | — | 30 |
| Dicumyl peroxide | 3 | 3 | 3 | 3 | 2 |
| Triethylaminetetraphenyl borate | — | — | 2 | — | 1 |
| Properties | | | | | |
| Glass transition temp. (°C.) | 170 | 172 | 179 | 178 | 175 |
| Flexural strength at 180° C. (kg/cm$^2$) | 450 | 470 | 520 | 490 | 460 |
| Retention of flexural strength after 30 days at 200° C. (%) | 100 | 100 | 100 | 100 | 100 |
| Bending strain (%) | 5.6 | 6.2 | 4.2 | 5.8 | 4.4 |

EXAMPLE 14

2,2-Bis[4-(4-aminophenoxy)phenyl]trifluoromethylpropane in an amount of 46.5 parts was dissolved in 200 parts of acetone and 22 parts of maleic anhydride was added thereto. The reaction was carried out at 3° to 5° C. for 2 hours under nitrogen stream with stirring. Precipitated resulting ether maleamic acid was separated by filtration. Thereafter, to the ether maleamic acid in an amount of 64.3 parts, 550 parts of acetic anhydride and 0.08 part of calcium acetate were added and the reaction was carried out at 60° to 80° C. for 2 hours.

After filtration, washing and drying, 62.6 parts of ether imide (e) was obtained.

The ether imide (e) had characteristic absorptions at 1230–1240 cm$^{-1}$ due to the ether linkage and at 1711 cm$^{-1}$ and 1778 cm$^{-1}$ due to the imide linkage in IR spectrum.

EXAMPLE 15

2,2-Bis[4-(4-aminophenoxy)phenyl]trifluoromethylpropane in an amount of 62.6 parts was dissolved in 200 parts of acetone and 36 parts of endomethylenetetrahydrophthalic anhydride dissolved in 200 parts of acetone was added thereto. The reaction was carried out at 3° to 5° C. for 3 hours with stirring. Precipitated resulting ether amic acid was separated by filtration. Thereafter, to the ether amic acid, 450 parts of acetic anhydride, 0.05 part of lithium acetate and 1 part of triethylamine were added and the reaction was carried out at 60° to 80° C. for 2 hours. After filtration, washing and drying, 92.5 parts of ether imide (f) was obtained.

The ether imide (f) had characteristic absorptions at 1230–1240 cm$^{-1}$ due to the ether linkage and at 1710 cm$^{-1}$ and 1781 cm$^{-1}$ due to the imide linkage in IR spectrum.

What is claimed is:

1. An ether imide of the formula:

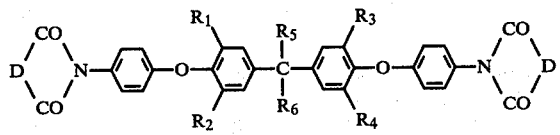

wherein $R_1$, $R_2$, $R_3$ and $R_4$ are independently hydrogen, a lower alkyl group, a lower alkoxy group, chlorine or bromine; $R_5$ and $R_6$ are independently hydrogen, a methyl group, an ethyl group, a trifluoromethyl group or a trichloromethyl group; and D is a bivalent organic group having 2 to 24 carbon atoms.

2. An ether imide according to claim 1, wherein $R_1$, $R_2$, $R_3$ and $R_4$ are hydrogen; $R_5$ and $R_6$ are independently a methyl group; and D is a group of the formula —CH═CH—,

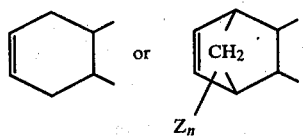

in which Z is hydrogen, halogen or a methyl group and n is an integer of 1 to 4.

3. An ether imide according to claim 1, wherein $R_1$, $R_2$, $R_3$ and $R_4$ are hydrogen; $R_5$ and $R_6$ are independently a trifluoromethyl group and D is a group of the formula —CH═CH—,

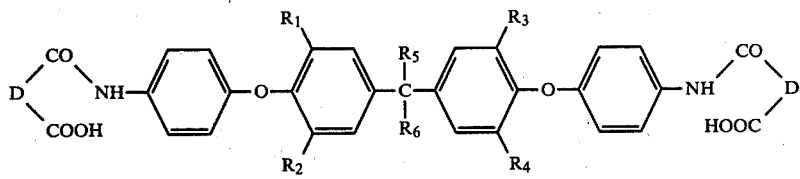

in which Z is hydrogen, halogen or a methyl group and n is an integer of 1 to 4.

4. An ether amic acid of the formula:

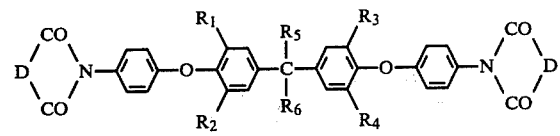

wherein $R_1$, $R_2$, $R_3$, and $R_4$ are independently hydrogen, a lower alkyl group, a lower alkoxy group, chlorine or bromine; $R_5$ and $R_6$ are independently hydrogen, a methyl group, an ethyl group, a trifluoromethyl group or a trichloromethyl group; and D is a bivalent organic group having 2 to 24 carbon atoms.

5. An ether amic acid according to claim 4, wherein $R_1$, $R_2$, $R_3$ and $R_4$ are hydrogen; $R_5$ and $R_6$ are independently a methyl group or a trifluoromethyl group; and D is a group of the formula —CH═CH—,

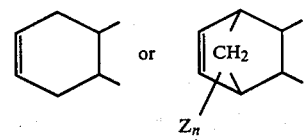

in which Z is hydrogen, halogen or a methyl group and n is an integer of 1 to 4.

6. A process for producing an ether imide of the formula:

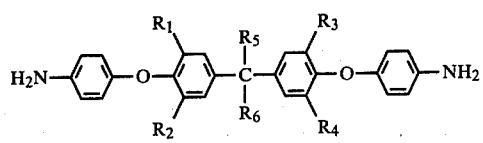

wherein $R_1$, $R_2$, $R_3$ and $R_4$ are independently hydrogen, a lower alkyl group, a lower alkoxy group, chlorine or bromine; $R_5$ and $R_6$ are independently hydrogen, a methyl group, an ethyl group, a trifluoromethyl group or a trichloromethyl group; and D is a bivalent organic group having 2 to 24 carbon atoms, which comprises reacting a diamine of the formula:

wherein $R_1$, $R_2$, $R_3$, $R_4$, $R_5$ and $R_6$ are as defined above, with an ethylenically unsaturated dicarboxylic acid anhydride of the formula:

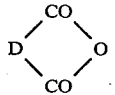

wherein D is as defined above, followed by ring-closing dehydration.

7. A process according to claim 6, wherein the reaction is carried out in two steps, the first step of which comprises contacting the diamine with the ethylenically unsaturated dicarboxylic acid anhydride in an organic solvent at a temperature of −10° to +40° C. to give an ether amic acid of the formula:

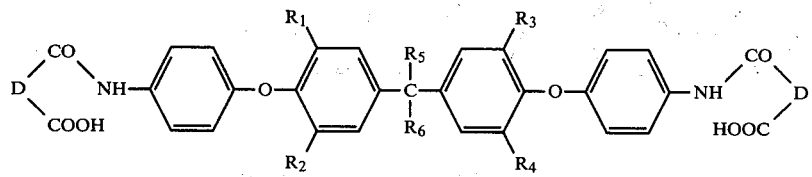

wherein $R_1$, $R_2$, $R_3$, $R_4$, $R_5$, $R_6$ and D are as defined in claim 6, and the second step of which comprises subjecting the ether amic acid to ring closing dehydration.

8. A process for producing an ether amic acid of the formula:

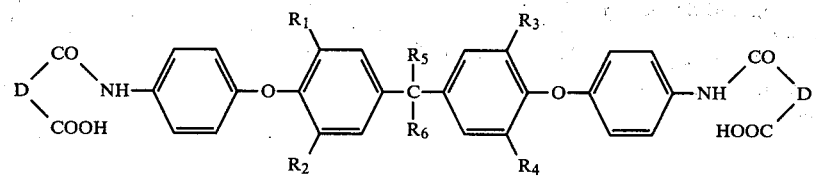

wherein $R_1$, $R_2$, $R_3$ and $R_4$ are independently hydrogen, a lower alkyl group, a lower alkoxy group, chlorine or bromine; $R_5$ and $R_6$ are independently hydrogen, a methyl group, an ethyl group, a trifluoromethyl group or a trichloromethyl group; and D is a bivalent organic group having 2 to 24 carbon atoms, which comprises contacting a diamine of the formula:

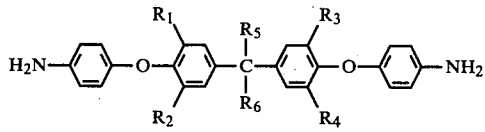

wherein $R_1$, $R_2$, $R_3$, $R_4$, $R_5$ and $R_6$ are as defined above, with an ethylenically unsaturated dicarboxylic acid anhydride of the formula:

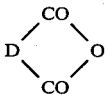

wherein D is as defined above, in an organic solvent at a temperature of −10° to +40° C.

9. A process according to claim 6 or 8, wherein the diamine is at least one member selected from the group consisting of 2,2-bis[4-(4-aminophenoxy)phenyl]propane, 2,2-bis[3-methyl-(4-aminophenoxy)phenyl]propane, 2,2-bis[3-butyl-4-(4-aminophenoxy)phenyl]propane and 2,2-bis[3-ethyl-4-(4-aminophenoxy)phenyl]propane and the bivalent ethylenically unsaturated dicarboxylic acid anhydride is at least one member selected from the group consisting of maleic anhydride, endomethylenetetrahydrophthalic anhydride, methylendomethylenetetrahydrophthalic anhydride and tetrahydrophthalic anhydride.

10. A process according to claim 6, wherein $R_1$, $R_2$, $R_3$ and $R_4$ are hydrogen; $R_5$ and $R_6$ are independently a methyl group or a trifluoromethyl group; and D is a group of the formula —CH=CH—,

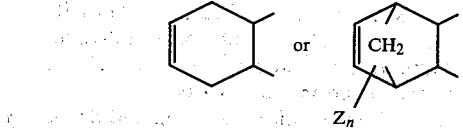

in which Z is hydrogen, halogen or a methyl group and n is an integer of 1 to 4.

11. A process according to claim 8, wherein $R_1$, $R_2$, $R_3$ and $R_4$ are hydrogen; $R_5$ and $R_6$ are independently a methyl group or a trifluoromethyl group; and D is a group of the formula —CH=CH—,

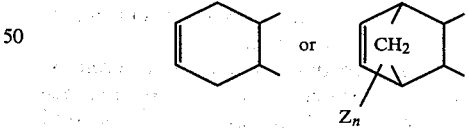

in which Z is hydrogen, halogen or a methyl group and n is an integer of 1 to 4.

12. An ether imide according to claim 1, wherein $R_1$, $R_2$, $R_3$ and $R_4$ are independently hydrogen; $R_5$ and $R_6$ are independently a methyl group and D is a —CH=CH— group.

13. An ether imide according to claim 1, wherein $R_1$, $R_2$, $R_3$, $R_4$, $R_5$ and $R_6$ are independently hydrogen and D is a —CH=CH— group.

* * * * *